United States Patent [19]

Chernack

[11] Patent Number: 4,869,720
[45] Date of Patent: Sep. 26, 1989

[54] HYPODERMIC SYRINGE ASSEMBLY
[75] Inventor: Milton P. Chernack, West Hempstead, N.Y.
[73] Assignee: E-Z-EM, Inc., Westbury, N.Y.
[21] Appl. No.: 190,646
[22] Filed: May 5, 1988
[51] Int. Cl.⁴ .......................................... A61M 5/315
[52] U.S. Cl. ................................................... 604/228
[58] Field of Search ................ 604/228, 229, 218, 187

[56] References Cited
U.S. PATENT DOCUMENTS
4,677,980  7/1987  Reilly et al. ................... 604/228 X
4,705,509 11/1987  Stade .............................. 604/228 X Primary Examiner—John D. Yasko
Attorney, Agent, or Firm—McAulay, Fisher, Nissen & Goldberg

[57] ABSTRACT

A hypodermic syringe assembly includes an elongated container and a cup shape molded piston longitudinal movable in the container. The container has a sidewall, a needle receiving end, and a piston receiving end which terminates in a rim. The piston has an open rear end with at least three equally spaced integral hinged tabs therearound. The piston has a first position partially inserted at the container rear where the tabs extend radially outward from the container adjacent its rear end. The piston in this position can receive a disc shaped plunger head. The piston has a second position fully inserted in the container where the tabs are rotated about their hinges and extend radially inward within the container. In this position the piston tabs hold a disc shaped plunger head within the piston. The piston has a third position partially extended out of the rim of the dispensing container. In this position the tabs are rotated about the hinges and extend radially outward sufficient to permit the plunger head to withdraw from the piston. The sidewall of the dispensing container holds the tabs in a radially inward position in all fully inserted longitudinal positions of the piston.

14 Claims, 4 Drawing Sheets

HYPODERMIC SYRINGE ASSEMBLY

BACKGROUND OF THE INVENTION

This invention relates to a hypodermic syringe assembly.

Many different types of hypodermic syringe assemblies are known in the art. Most of these assemblies use an elongate dispensing container in conjunction with a piston which is longitudinally movable within the container. Additionally, many of these syringe assemblies include a separate plunger mechanism. Examples of such prior art syringe assemblies include U.S. Pat. No. 2,586,068 to Lockhart; U.S. Pat. No. 2,688,325 to Lockhart; U.S. Pat. No. 3,874,382 to Nogier et al; U.S. Pat. No. 4,677,980 to Reilly et al and U.S. Pat. No. 3,672,368 to Schwarz.

When designing a syringe assembly it is sometimes desirable to have the plunger and piston capable of moving as a unit in both directions within the container. The Schwarz patent, in FIG. 5 thereof, discloses one method of doing this. The Schwarz patent uses claw shaped elastomeric extensions to engage a circumferential groove in a plunger so that the plunger and the piston can move together within the syringe container.

Although the arrangement shown in Schwarz creates good attachment between the plunger and the piston, it is an expensive arrangement due to the materials used.

Depending upon the application to which a syringe assembly will be used it may be desirable to have parts of the assembly disposable while other parts are not. If portions of a syringe assembly are disposable it is of course desirable to have these portions relatively inexpensive to manufacture. Further, any portions of the assembly which are to be reused must be kept from contact with any material which must be sterile.

Accordingly, it is a purpose of this invention to provide a hypodermic syringe assembly in which the piston is capable of locking to a plunger.

Yet a further purpose of this invention is to provide such an assembly which is relatively inexpensive to manufacture.

Another purpose of the invention is to provide such an assembly wherein the syringe container and piston are disposable and wherein the plunger to be used therewith is meant to be reused.

BRIEF DESCRIPTION

One embodiment of this invention involves a hypodermic syringe assembly including an elongated dispensing container with a central elongated axis and a sidewall radially outward of the axis. The container has a needle receiving forward end and piston receiving rearward end. A cup shaped molded piston is mounted for longitudinal motion in the container. The piston has an open rear end adapted to receive a disc shaped plunger head, a sidewall in sealing relationship with the sidewall of the dispensing container, and at least three equally spaced integral hinged holding tabs around the perimeter of the rear end of the piston.

The piston has a first position partially inserted in the container at the container rear end wherein the tabs extend radially outward from the container adjacent to the container back end. The piston in this position is capable of receiving the plunger head.

The piston has a second position fully inserted in the container with the tabs rotated about the hinges to extend radially inward within the container. In this position the tabs hold the plunger head within the piston.

The piston has a third position partially extended out of the container rim with each tab rotated about its hinge to extend radially outward sufficiently to permit the plunger head to be withdrawn from the piston.

The piston when fully inserted in the container lockingly holds the plunger head to allow the piston and plunger to move back and forth as a unit in the container.

DETAILED DESCRIPTION OF THE PREFERRED EMBODIMENT

Figure 1:
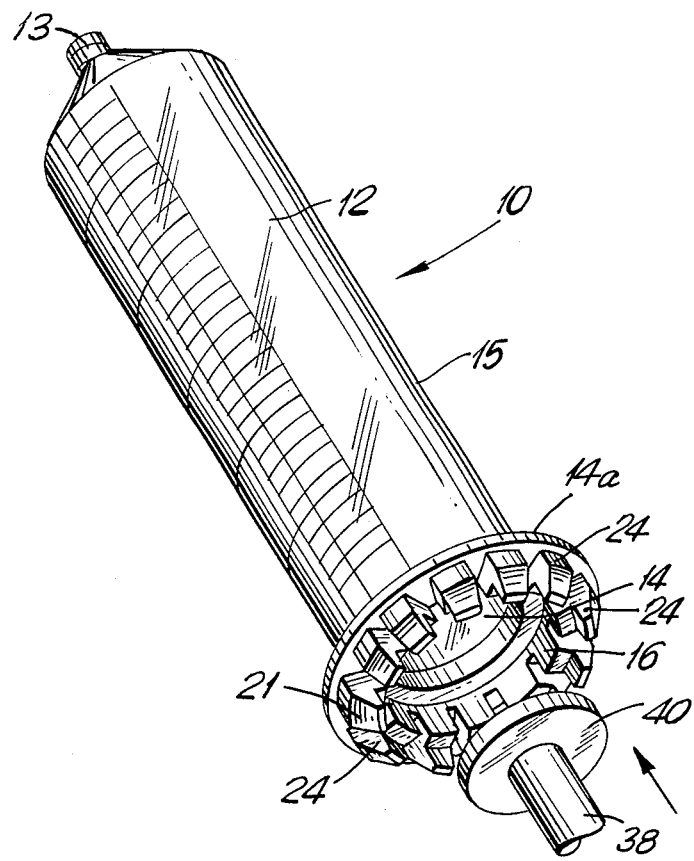
FIG. 1 is a perspective view of the hypodermic syringe assembly of the present invention showing the piston 16 in its initial position before the plunger 38 is connected thereto.

Referring now to the drawings, the reference numeral 10 denotes the hypodermic syringe assembly of the present invention. Assembly 10 includes an elongated dispensing container 12 with a central elongate axis and a sidewall 15 radially outward of this axis. The container has a needle receiving end 13 and a plunger receiving end 14. The plunger receiving end terminates in a rim 14a. The needle is not shown.

A molded plastic piston 16 is associated with container 12. Piston 16 has a closed forward 18 and an open rear end 20. The forward and rear ends of the piston are connected to one another by generally annular sidewall 22.

Ten equally spaced apart tabs 24 are integrally molded parts of the piston 16 and are at the rear end 20 of the piston. Each tab 24 is connected to the main body of the piston by an integrally molded plastic hinge 25.

An elongated plunger 38 is provided for association with piston 16. The plunger 38 has a disc shaped plunger head 40. The plunger 38 also has a rear end (not shown). It is contemplated that the rear end of the piston will be connected to an infusion pump which can be used to control the movement of the plunger 38.

Figure 2:
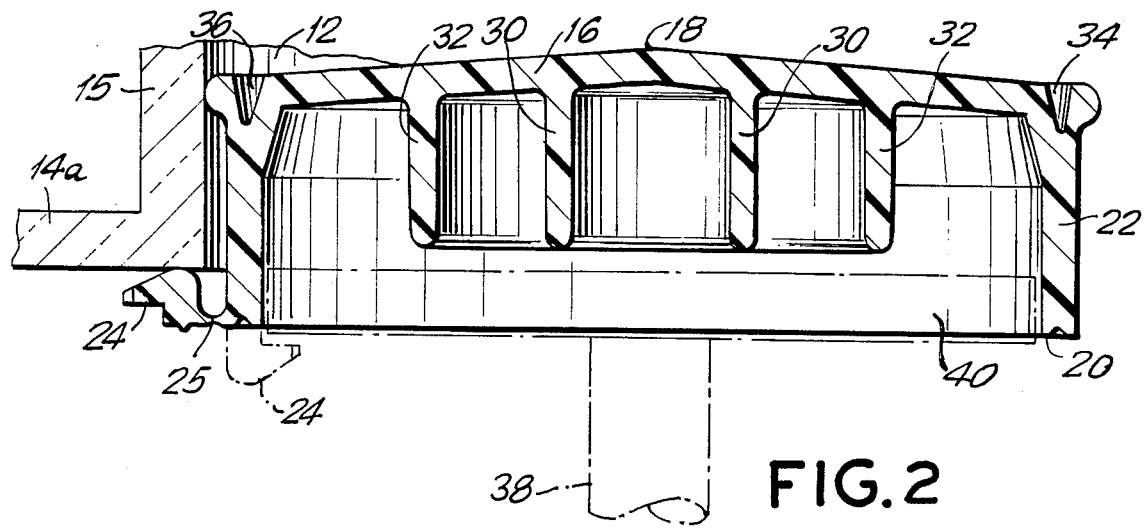
FIG. 2 is a longitudinal cross-sectional view of the FIG. 1 assembly showing the piston tab 24 before it rotates about its hinge 25 and also showing the piston tab, in phantom, after it has so rotated.
Figure 3:
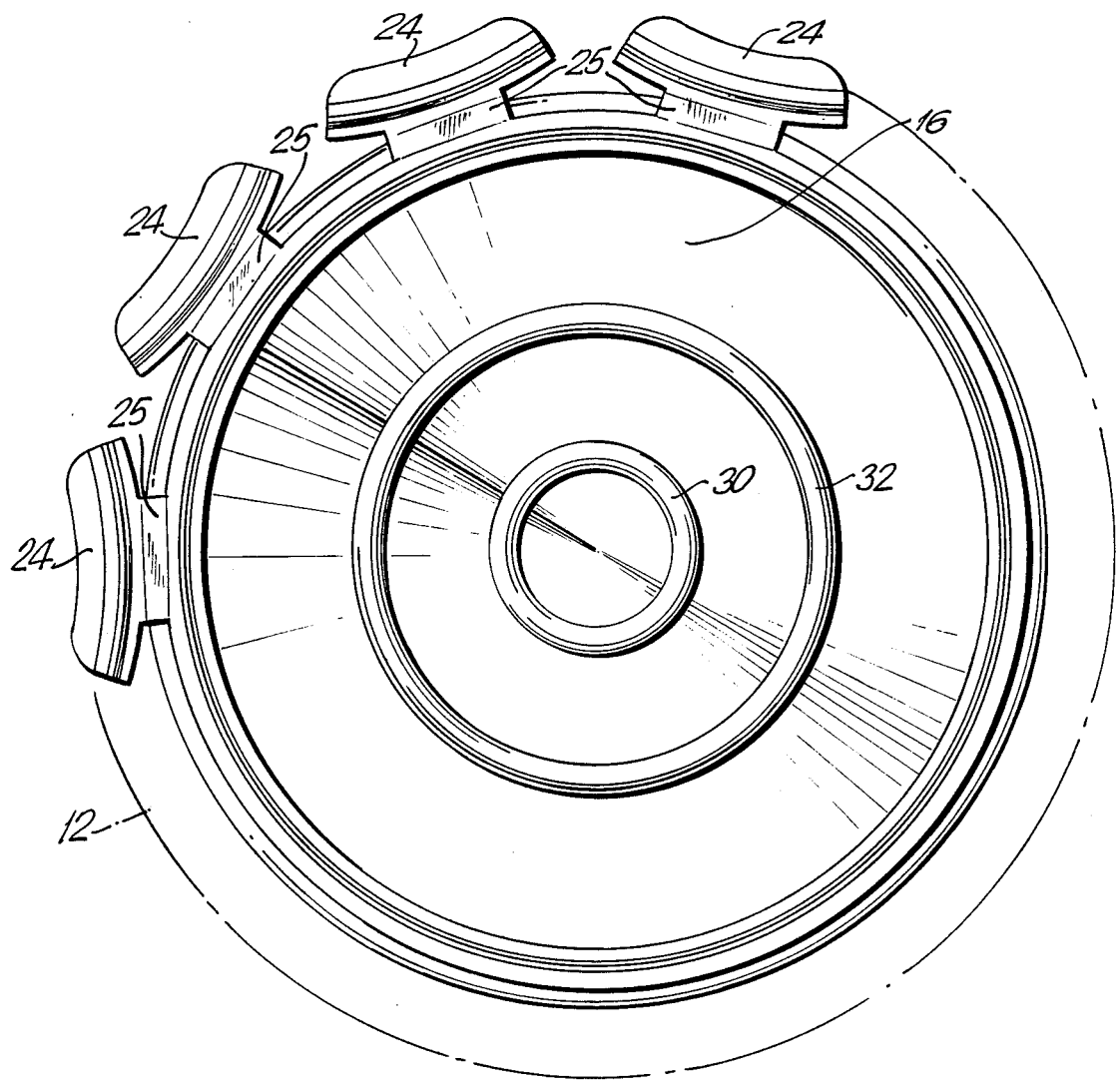
FIG. 3 is a plan view of the piston of the FIG. 1 assembly.

Piston 16, as best seen in FIGS. 1 and 2, has a first position where it is partially inserted in the rear of dispensing container 12. In said first position each of the tabs 24 extends radially outward from the container adjacent the rear end thereof. Piston 16 in said first position is capable of receiving disc shaped plunger head 40.

Figure 4:
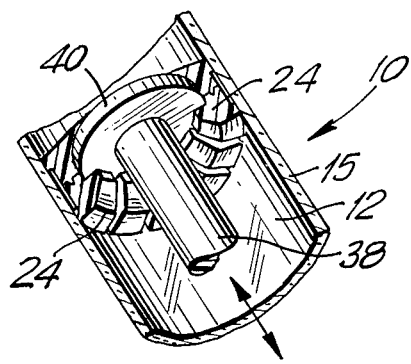
FIG. 4 is a broken away perspective view of the FIG. 1 assembly showing the piston in its inserted position with the plunger connected thereto.
Figure 5:
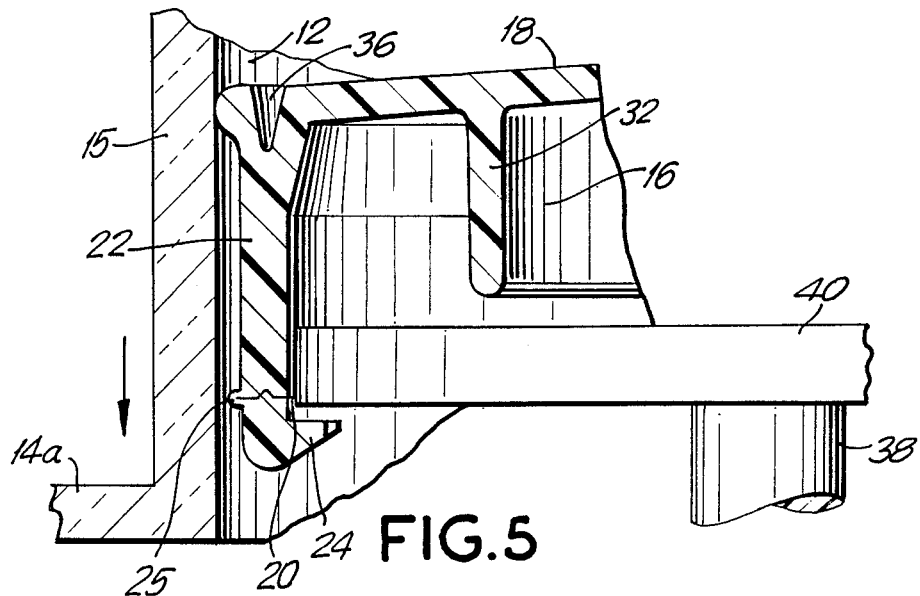
FIG. 5 is a partial sectional view of the FIG. 4 assembly showing the piston tabs rotated about their hinges when the piston in its inserted position.

Piston 16 has a second position, as best seen in FIGS. 4 and 5. When piston 16 is in said second position, it is fully inserted in the container 12. When piston 16 is in said second position, the tabs 24 are rotated about their hinges 25 and extend radially inward within the container. The tabs 24 in this position are capable of holding disc shaped plunger head 40 within piston 16. In this second position the container sidewall 15 holds tabs 24 in their radially inward position.

Figure 6:
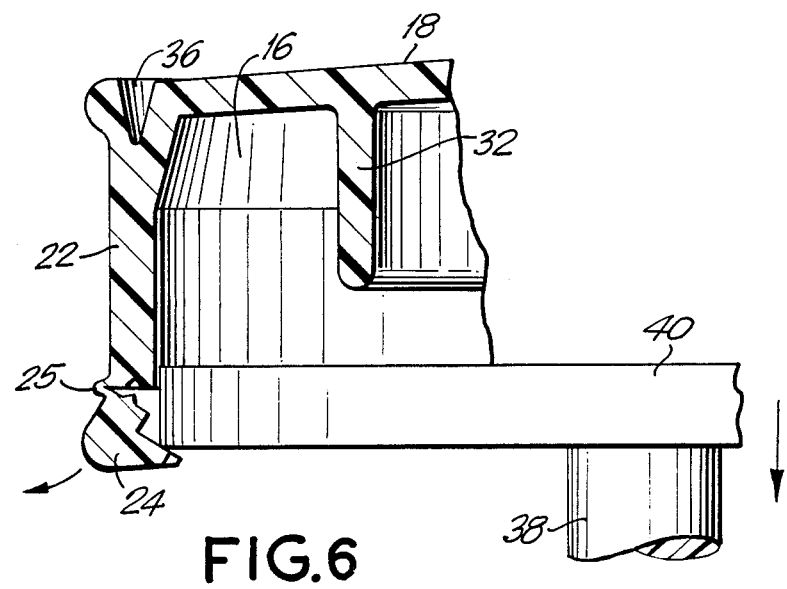
FIG. 6 is a view analogous to FIG. 5 but showing the piston in its retracted position as the plunger clears the rim of the syringe.

Piston 16 has a third position, as best seen in FIG. 6. In this position piston 16 partially extends out of container rim 14a. In this position tabs 24 are rotated about hinges 25 to extend radially outward sufficiently to permit plunger head 40 to be withdrawn from piston 16.

In use assembly 10 works as follows. The disc shaped plunger head 40 is forced longitudinally against the piston 16 when the piston is in its first position. This seats the plunger head 40 within piston 16 pushing piston 16 forward to thus cause tabs 24 to pivot 180° about the rear end 14 of the container sidewall 15 and to rotate on their integral hinges 25 to hold the plunger head and permit full insertion of the piston into the container. The piston is thus moved from its first to its second position.

At a later time when it is desired to withdraw the plunger head from the piston, the piston and plunger are moved in the container until the piston is in its third position hereto described.

When piston 16 is in its second position it lockingly connects to plunger head 40 so that the two can move as a unit within container 12. Further, in this second position piston 16 forms a fluid tight seal with the container sidewall which prevents plunger head 40 from having contact with any material held within container 12.

Piston 16 is formed with two concentric spaced apart stabilizing rings 30 and 32 inboard of the piston annular sidewall 22. The forward end 28 of piston 16 is formed with at least two notches 34, 36 therein. Notches 34 and 36 permit piston 16 to more easily fit within container portion 12 and to have a sealing relationship with the sidewall of the dispensing container.

Piston 16 may be formed of any appropriate non-elastomeric material and in one embodiment of the present invention, piston 16 is formed of polypropylene which is a relatively inexpensive material.

In one embodiment of this invention, the elongated container portion 12 has an inner diameter of about 1.8 inches (4.5 centimeters). The front end 18 of piston 16 has a diameter of about 1.84 inches (4.67 cm.). Due in part to the two notches 34 and 36 and in part to the nature of the material from which the piston is formed, the diameter of the front end of the piston is compressible to about 1.76 inches (4.47 cm.) which is also the diameter of the rear end 20 of the piston.

The tabs 24 when in their closed position are separated from one another by about 0.05 inches (0.127 cm.). The hinges 25 each have a length of about 0.250 inches (0.635 cm.).

It is contemplated that the piston, as molded, will have the tabs in the position shown when the piston is its first position. It is further contemplated that the piston when in its first position, partially inserted in the elongated container, will be packaged with the container in a sterile packaging. When it is desired to use the syringe assembly of the present invention, the sterilely packaged piston and container are opened and the disc shaped plunger head 40 moved as heretofore described to force piston 16 from its first position to its second position. It is contemplated that syringe assembly 10 will be used to inject a variety of dye materials for radiological examinations. It is further contemplated that elongated container 12 and piston 16 will be disposable to insure sterility. However, it is contemplated that plunger 38 will be reused as it is connected to expensive machinery and as it is never in contact with the sterile material.

Figure 7:
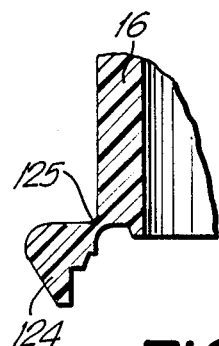
FIG. 7 is a sectional view of an alternative embodiment of the piston tab and hinge used in the assembly of the present invention.
Figure 8:
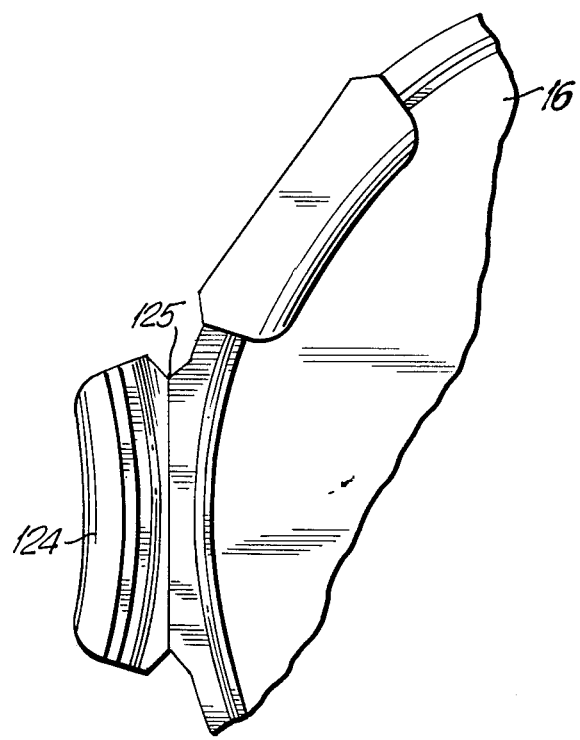
FIG. 8 is a plan view of the FIG. 7 piston tab and hinge.

Another embodiment of the invention is shown in FIGS. 7 and 8. Ten equally spaced apart tabs 124 are integrally molded parts of piston 16. Each tab 124 is connected to the main body of the piston by an integrally molded plastic hinge 125. Tabs 124 rotate about their hinges 125 in a manner substantially similar to the manner in which tabs 24 rotate about hinges 25. However in the embodiment shown in FIGS. 7 and 8 when disc shaped plunger head 40 is forced longitudinally against piston 16 to seat the plunger head within the piston and the piston 16 is thus pushed forward tabs 124 pivot 90 degrees about the rear end 14 of the container sidewall 15. Hinges 125, in contrast to hinges 25 each have a length of about 0.420 inches (1.07 cm.).

Piston 16, because of the material from which it is formed, allows assembly 10 to be relatively inexpensive which thus permits disposability of the container and piston. At the same time, if at least three equally spaced hinges are provided, the connection between the piston and the disc shaped plunger head is sufficient to avoid problems of slippage during any procedure. Because of the fluid tight seal formed between the piston and the container sidewall the more expensive plunger can be reused without compromising the sterility of any procedure or material.

What is claimed is:

1. A hypodermic syringe assembly comprising:
   an elongate dispensing container having a central elongate axis and a sidewall radially outward of said axis,
   said container having a needle receiving forward end and a piston receiving rearward end terminating in a rim,
   a cup shaped molded plastic piston mounted for longitudinal motion in said container, said piston having an open rear end adapted to receive a disc shaped plunger head, and a closed front end,
   said piston having a sidewall in sealing relationship with the sidewall of said dispensing container,
   said piston having at least three integral hinged holding tabs substantially equally spaced around the perimeter of the rear end of said sidewall of said piston,
   said piston having a first position partially inserted in said container at the rear of said dispensing container wherein each of said tabs extends radially outward from said container adjacent to the back end of said container,
   said piston in said first position capable of receiving a plunger head,
   said piston having a second position fully inserted in said container wherein said tabs are rotated about said hinges and extend radially inward within said container,
   said tabs of said piston in said second position capable of holding a plunger head within said piston,
   said piston having a third position partially extended out of said rim of said dispensing container wherein each of said tabs are rotated about said hinges to extend radially outward sufficiently to permit a plunger head to withdraw from said piston, said sidewall of said dispensing container holding said tabs in said radially inward position in all fully inserted longitudinal positions of said piston, whereby a plunger head forced longitudinally forward against said piston in said first position will seat within said piston and push said piston forward causing said hinged tabs to pivot about the rear end of said container sidewall and rotate on their integral hinges to hold the plunger head and permit full insertion of the piston.

2. The syringe assembly of claim 1 having ten equally spaced hinged holding tabs.

3. The syringe of claim 1 wherein the piston is formed of a non-elastomeric material.

4. The syringe of claim 1 wherein the piston is formed of polypropylene.

5. The syringe of claim 2 wherein the piston is formed of non-elastomeric material.

6. The syringe of claim 2 where the piston is formed of polypropylene.

7. The syringe assembly of claim 1 wherein said hinged tabs are capable of at least 90° movement.

8. The syringe assembly of claim 1 wherein said hinged tabs are capable of 180° movement.

9. The syringe assembly of claim 2 wherein said hinged tabs are capable of at least 90° movement.

10. The syringe assembly of claim 2 wherein said hinged tabs are capable of 180° movement.

11. The syringe assembly of claim 1 wherein said piston is formed with two spaced apart concentric stabilizing rings.

12. The syringe assembly of claim 1 wherein the front end of said piston is formed with at least two small notches therein said notches allowing said piston to more easily fit within said container body and to more effectively create a fluid tight seal therein.

13. The syringe assembly of claim 1 wherein said piston and said elongated container are disposable and wherein said plunger is reusable.

14. The syringe assembly of claim 2 wherein the inner diameter of the elongated container is about 1.8 inches, the uncompressed diameter of said forward end of said piston is about 1.84 inches, the compressed diameter of said forward end of said piston is about 1.76 inches each tab hinge is about 0.420 inches long and wherein said hinged tabs when in said closed position are spaced apart by about 0.050 inches.

* * * * *